United States Patent [19]

Klevan et al.

[11] Patent Number: 4,828,979

[45] Date of Patent: May 9, 1989

[54] NUCLEOTIDE ANALOGS FOR NUCLEIC ACID LABELING AND DETECTION

[75] Inventors: Leonard Klevan, Washington, D.C.; Gulilat Gebeyehu, Silver Spring; Prasad Y. Rao, Damascus, both of Md.

[73] Assignee: Life Technologies, Inc., Gaithersburg, Md.

[21] Appl. No.: 669,334

[22] Filed: Nov. 8, 1984

[51] Int. Cl.$^4$ .................... C12Q 1/68; C07H 19/10; C07H 19/20
[52] U.S. Cl. .......................... 435/6; 536/27; 536/28; 536/29
[58] Field of Search .................. 536/27, 28, 29; 435/6

[56] References Cited

U.S. PATENT DOCUMENTS

| | | | |
|---|---|---|---|
| 4,038,480 | 7/1977 | Robins et al. | 536/28 |
| 4,088,639 | 5/1978 | Rapelli et al. | 536/28 |
| 4,213,893 | 7/1980 | Carrico et al. | 536/27 |
| 4,255,566 | 3/1981 | Carrico et al. | 536/28 |
| 4,443,594 | 4/1984 | Buckmann | 536/27 |
| 4,460,772 | 7/1984 | Benovic et al. | 536/27 |
| 4,707,440 | 11/1987 | Stavrianopoulos . | |

FOREIGN PATENT DOCUMENTS

| | | | |
|---|---|---|---|
| 0063879 | 11/1982 | European Pat. Off. | 536/29 |
| 0133283 | 11/1978 | Japan | 536/27 |
| 0011999 | 1/1982 | Japan | 536/27 |
| 0096610 | 5/1985 | Japan | 536/28 |
| 1552607 | 9/1979 | United Kingdom | 536/27 |

OTHER PUBLICATIONS

Murasugi et al., DNA, vol. 3, No. 3 (Jul. 1984), pp. 269–277.
Guilford et al., Chemical Scripta (Sweden) 1972, 2(4), pp. 165–170.

Primary Examiner—Johnnie R. Brown
Assistant Examiner—Jenny Tou
Attorney, Agent, or Firm—D. Peter Hochberg; Mark M. Kusner; Louis J. Weisz

[57] ABSTRACT

Nucleotide analogs, modified by the attachment at hydrogen bonding positions of linker groups, that is, the 6-position of adenine, 4-position of cytosine, and 2-position of guanine, are prepared. Such analogs, alone or with reporter groups attached, may be incorporated into DNA probes which effectively hybridize to target DNA.

12 Claims, 7 Drawing Sheets

Bio-3-dATP   L-(CH$_2$)$_2$
Bio-7-dATP   L-(CH$_2$)$_6$
Bio-10-dATP  L-(CH$_2$)$_2$NHCO(CH$_2$)$_5$
Bio-14-dATP  L-(CH$_2$)$_6$NHCO(CH$_2$)$_5$
Bio-10'-dATP L- CH$_2$CONH(CH$_2$)$_6$
Bio-17-dATP  L- CH$_2$CONH(CH$_2$)$_6$NHCO(CH$_2$)$_5$

Bio-3-dCTP   L=(CH$_2$)$_2$
Bio-7-dCTP   L=(CH$_2$)$_6$
Bio-10-dCTP  L=(CH$_2$)$_2$NHCO(CH$_2$)$_5$
Bio-14-dCTP  L=(CH$_2$)$_6$NHCO(CH$_2$)$_5$

Bio-3-dATP   L=(CH₂)₂
Bio-7-dATP   L=(CH₂)₆
Bio-10-dATP  L=(CH₂)₂NHCO(CH₂)₅
Bio-14-dATP  L=(CH₂)₆NHCO(CH₂)₅
Bio-10'-dATP L=CH₂CONH(CH₂)₆
Bio-17-dATP  L=CH₂CONH(CH₂)₆NHCO(CH₂)₅

Fig. 1

Bio-3-dCTP   L=(CH₂)₂
Bio-7-dCTP   L=(CH₂)₆
Bio-10-dCTP  L=(CH₂)₂NHCO(CH₂)₅
Bio-14-dCTP  L=(CH₂)₆NHCO(CH₂)₅

NUCLEOTIDE ANALOGS FOR NUCLEIC ACID LABELING AND DETECTION

This invention relates to techniques of detecting the hybridization of nucleic acid probes to target nucleic acids. In particular, it relates to a method of biotinylating such probes so that biotin-avidin or biotin-streptavidin binding may be used to localize and detect the target.

BACKGROUND OF THE INVENTION

Nucleic acid hybridization has found widespread application in genetic research, biomedical research and clinical diagnostics. The development of a technology for "mixed phase hybridization" (hybridizing probes to immobilized target DNA) and for cloning of unique sequence genetic probes has lead to major advances in basic and applied areas of biochemistry and medicine (For a review see: Meinhoth, J. and Wahl, G., (1984) Analytical Biochemistry 138, 267-284). In the standard hybridization reaction, a radioisotope-labeled probe is annealed to a DNA or RNA sample which has been immobilized on an inert solid support. The detection of a radioactive signal by autoradiography indicates the presence or absence of the complementary nucleic acid sequence in the target sample. In the past, the potential health hazards, disposal problems and instability of radionucleotides have placed limitations on the use of nucleic acid probes. This has lead to great interest in the development of alternative DNA labeling and detection systems which do not contain the drawbacks inherent in the use of radioisotopes.

The development of a nonradioactive DNA detection system requires a method to label the nucleic acid probe and a means to recognize and detect the annealed probe-target hybrid. The high binding constant and specificity of biotin for avidin or streptavidin (reviewed in Green, M., (1975) Advances in Protein Chemistry, 29, 85-133) have been used in different systems to localize and detect a wide range of target molecules.

The principle of the biotin-avidin interaction as the basis of probe-ligand interactions in molecular biology was reviewed by Bayer and Wilchek in 1979: "Thus (in addition to biotin-requiring enzymes) biotin-derivatized hormones, phages, lectins, antibodies and other binding proteins can interact with avidin; and if the avidin is immobilized or covalently bound to a potentially perceptible probe, the avidin-biotin complex can be used for the localization or isolation of the compounds above and/or their receptors" (Bayer, E. A. and Wilchek, M. (1979), Methods in Biochemical Analysis 26, 1-45). This principle is further described in U.S. Pat. No. 4,228,237 (Hevey, R. C. and Malmros, M. K., Oct. 14, 1980) in wnich an avidin-coupled signaling enzyme is used to recognize a biotin-labeled reagent which will specifically bind to the ligand in question.

Other examples of biotin-avidin interactions as applied to probes are contained within an article by Langer et al. (Langer, P. R., Waldrop, A. A. and Ward, D. C. (1981) Proc. Natl. Acad. Sci., USA 78 6633-6637), who describe the synthesis of biotin-UTP and biotin-dUTP analogs which are substrates for a variety of RNA and DNA polymerases. The disclosures in this publication were further set forth in European Patent Application EP No. A200063879, in which it is claimed that biotin may be covalently linked to the 8-position of a purine base or the 5-position of a pyrimidine base in a nucleoside triphosphate.

However, it is stated by Ward, et al., in that application that ". . . probe moieties should not be placed on ring positions that sterically, or otherwise, interfere with the normal Watson-Crick hydrogen bonding potential of the bases. Otherwise, the substitutents will yield compounds that are inactive as polymerase substrates . . . Normally, such considerations limit substitution positions to the 5-position of a pyrimidine and the 7-position of a purine or a 7-deazapurine." (The Ward disclosure and claims show that the 8-position of a purine was intended.) This statement reflects the common supposition that if labels are attached to nucleotides at the hydrogen bonding positions the modified nucleotides cannot be useful in probes.

Notwithstanding the teachings of Ward and others, the inventors herein have discovered that nucleotide analogs in which biotin is attached at the hydrogen bonding position of the purine or pyrimidine base may be iccorporated into probes. Moreover, probes labelled in this manner will still hybridize to "target" DNA in highly sensitive detection protocols. This result has occasioned the production of a new class of labeled nucleotides, the usefulness of which was hitherto unsuspected.

SUMMARY OF THE INVENTION

According to thepresent invention, dATP and dCTP are modified at the amino-nitrogen at the 6- and 4-positions, respectively, through a linker arm that varies in length from 3 to 17 atoms. dGTP may be similarly modified at the 2-position. Nucleotides labelled thereby with biotin are stable for at least one year, are inexpensive to prepare and are substrates for *E. coli* DNA polymerase I. Nucleic acid probes incorporating these analogs may be prepared by standard nick-translation protocols and employed for non-radioactive DNA detection when used with streptavidin-conjugated enzymes or enzyme polymers.

The same methods of synthesis may be used to prepare unlabelled nucleotide precursors which contain a linking group at the positions mentioned. The label or reporter group is added after incorporation. "Chain terminator" nucleotide analogs may also be synthesized.

Accordingly, it is an object of the present invention to provide improved methods for detecting the presence of specific polynucleotides or nucleic acids.

Another object of the present invention is to provide a novel means of labelling polynucleotides for detection of specific sequences, for use as probes, and the like.

It is another object of the present invention to provide a novel class of nucleotide analogs which may be incorporated into nucleic acids without interfering with hybridization to complementary nucleic acids.

A still further object of the invention is to provide nucleotide analogs which may be linked uniquely to biotin before or after incorporation into nucleic acids.

Other objects will be seen from the description of preferred embodiments and claims, as explained by the entire specification and the Figures, in which

GENERAL METHODS OF SYNTHESIS AND USE

We have used two approaches for the synthesis of dATP analogs. In the first, a modifiable amino group is introduced via reaction of chloropurine with diamino alkane. In the second approach, the amino group at the 6 position is alkylated by a modifiable group. In the case of dCTP, a modifiable amino group is introduced by transamination. dGTP analogs may also be prepared by the reaction of diaminoalkane with 2-chloro-2'-deoxyinosine following a similar procedure to that described for dATP. In all cases the amino group involved in Watson-Crick hydrogen bonding is preferably modified.

For convenience, the following abbreviations will be used:

B-NHS: N-hydroxysuccinimide biotin ester
CAB-NHS: N-hydroxysuccinimide caproylamidobiotin ester
CDI: carbonyldiimidazole
EDC: ethyl dimethylaminopropyl carbodiimide
DAE: 1,2-diaminoethane
DAH: 1,6-diaminohexane
TEAB: triethylammonium bicarbonate

Synthesis of biotinylated dATP (FIGS. 2 and 3) and dGTP

In a first approach, the synthesis starts from the known compound 6-chloropurine-2'-deoxyriboside. This compound was prepared (FIG. 2, (1)) in about 70% yield from 2'-deoxyinosine by using Robins' procedure. (M. J. Robins & G. L. Basom in "Nucleic Acid Chemistry" p. 602 (1978) edited by Townsend & Tipson.) It was phosphorylated (FIG. 2, (2)) using $POCl_3$/$(EtO)_3PO$ (M. Yoshikawa, T. Kato & T. Takenishi, Tetrahedron Lett. 5095 (1967)) in the presence of 4 Å molecular sieves. The presence of molecular sieves is preferred since in their absence the reaction gives a mixture of products, the desired compound being only a minor component.

Figure 1:
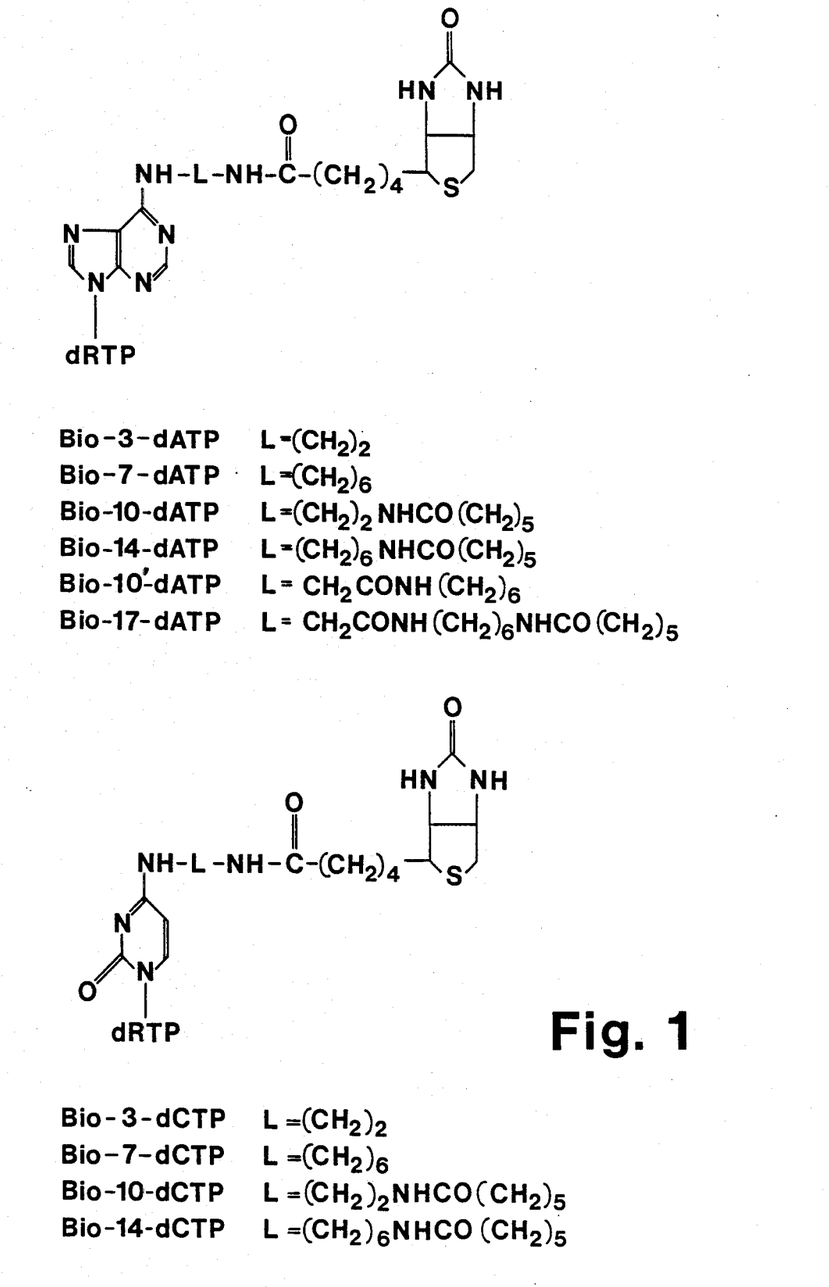
FIG. 1 is a schematic molecular representation of some typical compounds synthesized according to the present invention.
Figure 2:
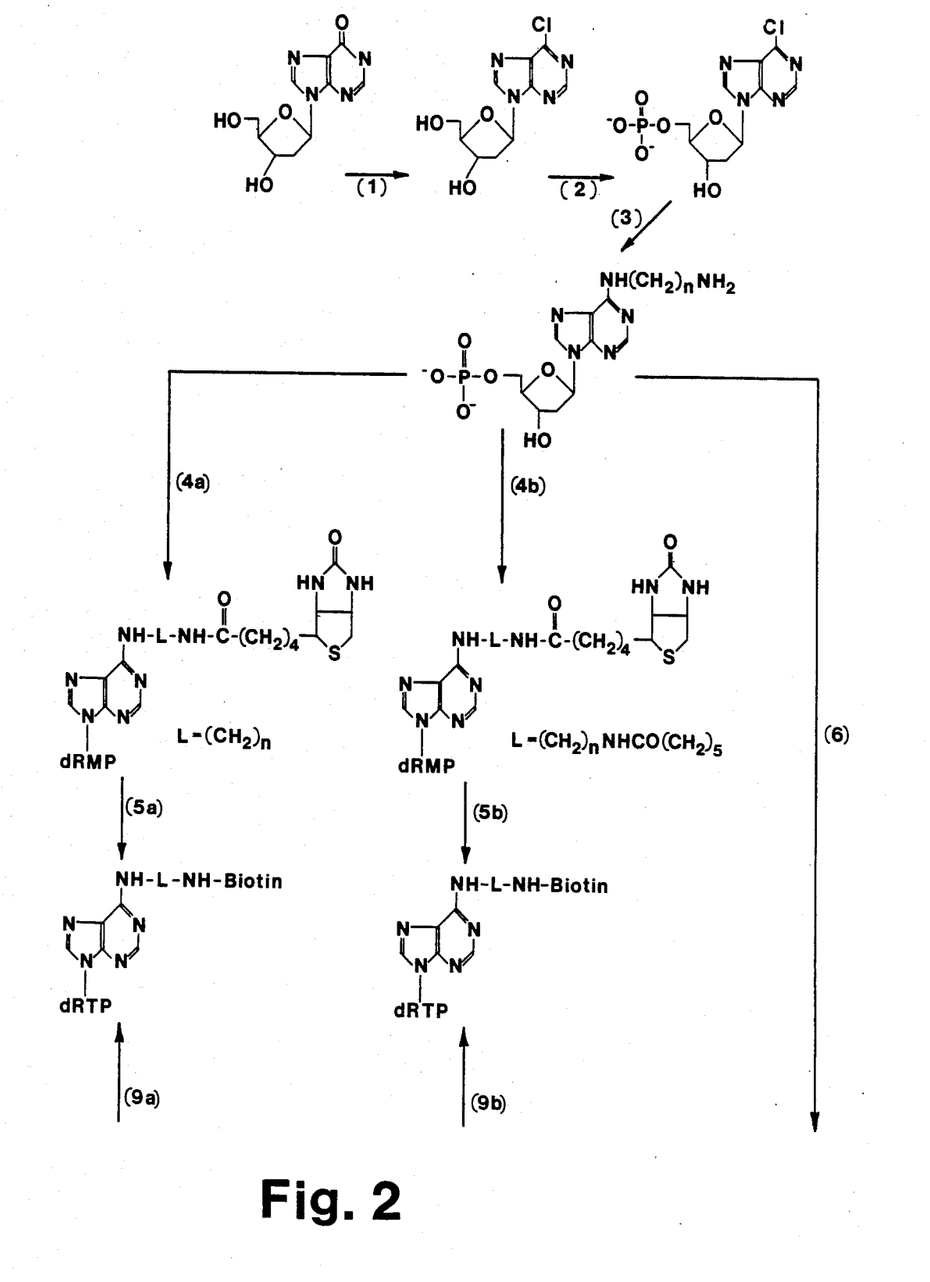
FIG. 2 is a schematic representation of syntheses of some of the dATP analogs of the present invention.
Figure 3:
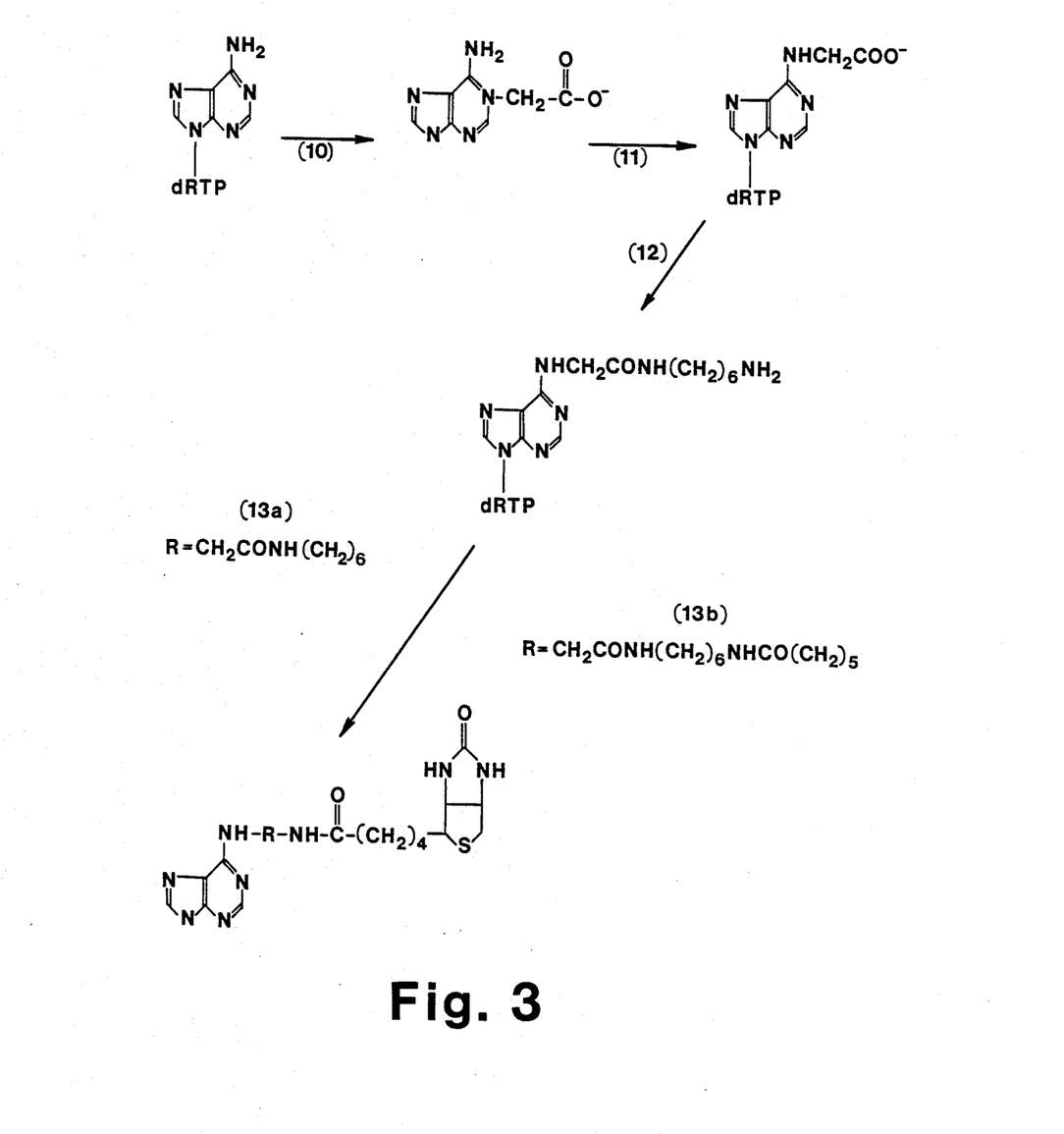
FIG. 3 is a schematic representation of other synthetic methods for dATP analogs of the present invention.

The resulting monophosphate was then treated (FIG. 2, (3)) with diaminoalkane to give the desired $N^6$-(n-aminoalkyl)dAMP. In our examples, DAE (n=2) and DAH (n=6) were employed, but n can range from 2 to 12, and probably beyond. $N^6$-(6-aminohexyl)dAMP was obtained 60–70% yield, whereas the yield of $N^6$-(2-aminoethyl) dAMP was very low. (The reaction condition was not maximized to increase the yield.)

The biotinylation (Ward et al., Proc. Natl. Acad. Sci. USA 78 6633 (1981)) was accomplished by treating the $N^6$-(aminoalkyl)dAMP with B-NHS (FIG. 2, (4a)), or CAB-NHS (FIG. 2, (4b)). (S. M. Costello, R. T. Felix & R. W. Giese, Clin. Chem. 25 1572 (1979). Bio-7-dAMP and Bio-14-dAMP were obtained in 70–90% yield. Bio-3-dAMP and Bio-10-dAMP were also obtained in high yield, about 50–80%. In place of CAB-NHS one may employ the biotin ester of any acid of the form $H_2N(CH_2)_mCOOH$ for m such that the total linker length does not exceed 26 atoms.

Finally the triphosphates were prepared (FIG. 2, (5a) and (5b)) by using the Hoard & Otts (D. E. Hoaro & D. G. Otts, J. Am. Chem. Soc. 87, 1785 (1965)) method. That is, the monophosphates were treated with CDI followed with tributylammonium pyrophosphate to give Bio-7-dATP, Bio-3-dATP, Bio-14-dATP and Bio-10-dATP. The yield varied between 30 and 80%.

The Bio-7-dATP was also prepared (FIG. 2, reactions (6)–(9)) from $N^6$-(6-aminohexyl)dATP. This approach is particularly useful in the synthesis of radiolabelled biotinylated nucleotides or for attachment of other detectable groups. Where it is desired to fully phosphorylate the precursor before labelling, it is preferred to protect the amino group during the phosphorylation step, as Trayer et al. (Trayer et al., Biochem J. 139, 609 (1974)) have reported that the application of the Hoard-Ott method on the ribose analog $N^6$-(6-aminohexyl)-AMP resulted in a complicated mixture and a low yield of the desired compound. Accordingly, the amino group in $N^6$-(6-aminohexyl)dAMP was protected with a trifluoro acetyl group by treatment (FIG. 2,(6)) with ethyl trifluorothioacetate according to the procedure of Trayer, et al., to give $N^6$-(6-Trifluoroacetamidohexyl)dAMP, which was then converted (FIG. 2,(7)) to the triphosphate by the Hoard & Ott method. Basic hydrolysis (pH 11) of the protecting group (FIG. 2,(8)) yielded $N^6$-(6-Aminohexyl)dATP. This was then treated with B-NHS to yield Bio-7-dATP, (FIG. 2, 9(a)), or, analogously, treatment with CAB-NHS will yield Bio-14-dATP (FIG. 2, 9(b)). Tritium labelled Bio-7-dATP was synthesized analogously by using tritium labelled biotin-NHS ester. (Commercial product from Amersham).

In the second approach, (see FIG. 3) dATP was alkylated (10) at the N-1 position with iodoacetic acid at pH 6.5 and subsequently rearranged (11) at pH 8.5, 90° C. to the N-6 position to yield $N^6$-carboxymethyl dATP. (M. Lindeberg and K. Mosback Eur. J. Biochem 53, 481 (1975)). That compound was then condensed (12) with diaminohexane using EDC, a water soluble coupling agent. Other diaminoalkanes with up to 12 carbon atoms may be employed. The aminohexyl adduct was then coupled with B-NHS (13a) or CAB-NHS (13b) to give the corresponding Bio-10'-dATP or Bio-17-dATP.

These compounds were also made by effecting the alkylation and the rearrangement on dAMP. The biotinylated compounds were then converted to Bio-10'-dATP and Bio-17-dATP respectively by using the Hoard-Ott method.

Generally the yield on the second approach is lower due to depurination on the first step.

The synthesis of dGTP analogs would start with 2-chloro-2'-deoxyinosine Phosphorylation of this compound by the modified Yoshikawa method followed by treatment with diaminoalkane will give the corresponding $N^2$(n-aminoalkyl)dGMP. This will then be subjected to the same treatment as in the case of $N^6$-(n-aminoalkyl)dAMP to obtain the corresponding biotinylated dGTP or the $N^2$(n-aminoalkyl)dGTP precursor.

Synthesis of biotinylated dCTP

Figure 4:
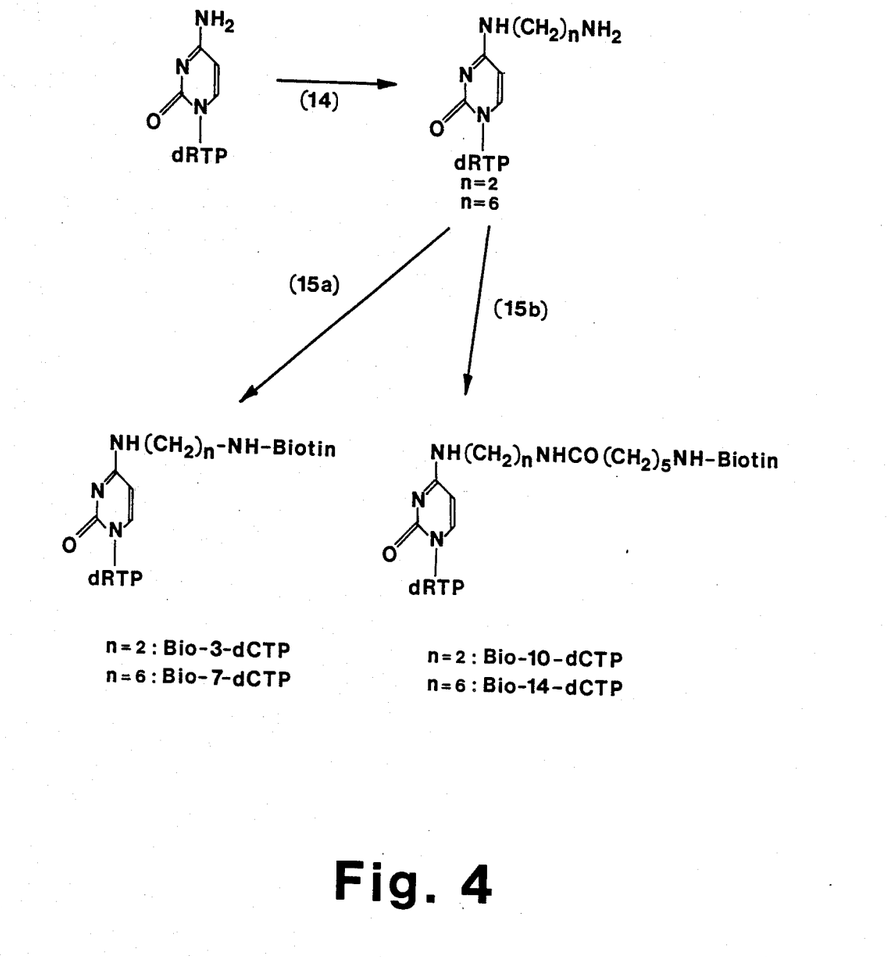
FIG. 4 is a schematic representation of a synthetic method for the dCTP analogs of the present invention.

The synthesis of biotinylated dCTP (FIG. 4) follows the procedure described by Draper (D. E. Draper, Nucleic Acid Res. 12 989 (1984)) where bisulfite-catalyzed transamination is effected at the N-4 position. Treatment of dCTP with DAE or DAH in the presence of bisulfite at a pH of about 5.5, followed by adjustment of the pH to about 8.5, (FIG. 4, (14)) gave $N^4$-(2-aminoethyl)dCTP or $N^4$-(6-aminohexyl)dCTP respectively. The yield in either case was less than 50%. The nucleotides are then treated (15(a),(b)) with B-NHS or CAB-NHS to give the desired compounds.

Use of these and analogous modified nucleotides

As will be seen from the experimental examples to follow, the modified nucleotides of the present invention may be incorporated into nucleic acids. Their presence is detectable with a high degree of sensitivity, and labelled probes may be used to detect a single-copy gene sequence using existing methods.

Using reactions 1-3 plus 6-8, reaction 14, or reactions 10-12, nucleotide-analog precursors of these compounds, (such as $N^6$-(6-aminohexyl)dATP) may also be synthesized. They may be directly incorporated into nucleic acid probes and then linked to reporter molecules, such as biotin, or activated enzymes (e.g., enzymes activated with amino reactive, bifunctional crosslinking reagents such as Bis(sulfosuccinimidyl)suberate or dimethyl suberimidate). Recently, it has been demonstrated that protein-linked single-stranded probes may be used in standard hybridization assays (Renz, M. and Kurz, C. (1984) Nucleic Acids Res. 12 3435-3444). It is also clear to one skilled in the art that other reporter groups such as tetramethylrhodamine isothiocyanate, fluorescein isothiocyanate or dimethylaminoazobenzene sulfonyl chloride may be condensed with the primary amino group of the nucleotide-analog precursors after incorporation into a nucleic acid (Richardson, R. W. and Gumport, R. I., (1983) Nucleic Acids Res. 11 6167-6184).

The same synthetic procedures reported above may also be used to synthesize the corresponding chain terminator nucleotides such as 3'-deoxynucleoside-5'-triphosphate analogs or 2', 3'-dideoxynucleoside-5'-triphosphate analogs. The 3'-deoxy analogs may be condensed, before or after the reporter group is added, with the 3' ends of a nucleic acid by chemical means or through the use of terminal deoxynucleotidyl transferase (TdT) (Tu, C.-P. D. and Cohen, S. P. (1980) Gene 10 177-183). This addition of a single biotin nucleotide to the 3'end of each strand of DNA will permit the labelling of nucleic acids for detection of specific gene sequences in biomedical and research applications.

The particular "linkers" we have described are presently preferred, as is their bonding to the label, or reporter group, by an amido group. However, the linker can be any suitable compound which does not interfere either chemically or sterically with the desired application; further examples will be evident to one skilled in the art. For practical purposes, its length (that is, the number of atoms between the amino group of the base and the reporter group) should not be more than about 26. A range of 3 to 17 is preferred. Our invention also contemplates the use of other bonding groups such as esters and thioesters. For example, the chloronucleotides can be treated with aminoalkanol (e.g. 6-aminohexanol) to give $N^6$-(n-hydroxyalkyl)dATP which can be esterified with biotin or longer chain analogs using standard coupling means such as dicyclohexyl carbodiimide. For the thioester, the chloronucleotide can be treated with aminoalkanethiol to yield $N^6$-(n-thioalkyl)dATP, which is esterified the same way.

EXAMPLES SHOWING PREFERRED EMBODIMENTS

Incorporation into Plasmid DNA of Biotinylated dATP Derivatives

The time course and levels of incorporation were studied as a function of linker size.

Using the BRL Nick Translation System, dATP and various derivatives were incorporated into plasmid DNA. The 400 $\mu$l reaction mixture contained 50 mM Tris-HCl (pH 7.8), 5 mM $MgCl_2$, 10 mM 2-mercaptoethanol, 10 $\mu$g/ml BSA, 20 $\mu$M each of dGTP, dCTP, dTTP and dATP or a dATP derivative, 4 $\mu$g of a 5.4 Kb plasmid, 10 $\mu$Ci of $^3$H-dGTP (12 Ci/mmole), 8 units of DNA polymerase I and 0.8 ng of DNase I. Reaction was carried out at 15° C.

At each time point of interest, 2 $\mu$l from the reaction mixture was withdrawn, spotted on glass fiber filters (GF/C), washed in 10% trichloroacetic acid (TCA) once and 5% TCA twice, and dried after washing in alcohol. The filters were counted in a liquid scintillation counter.

Figure 5:
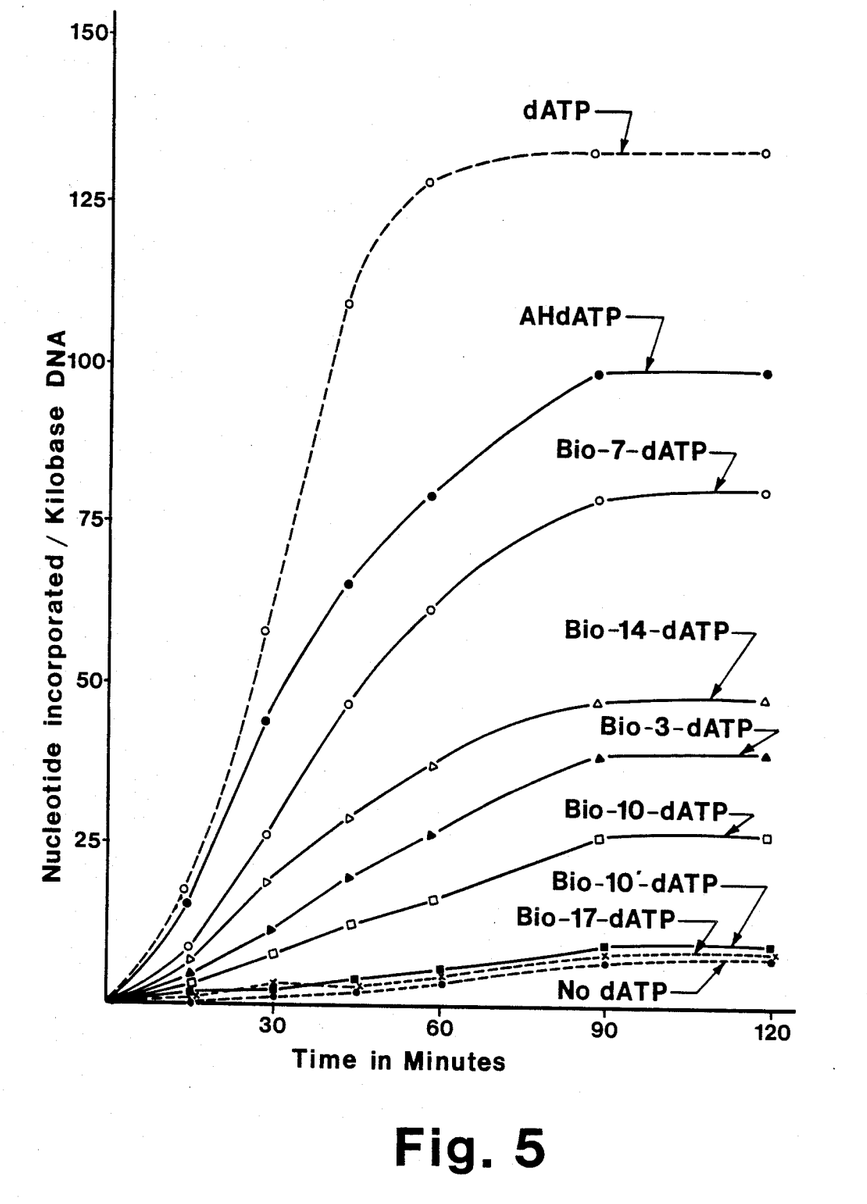
FIG. 5 is a graph showing the incorporation into DNA of some dATP analogs of the present invention, as a function of time.

FIG. 5 shows the time course of incorporation, given as labelled nucleotide incorporated per kilobase of DNA, when either dATP, a derivative precursor $N^6$-(6-aminohexyl)dATP, biotinylated dATP with various linker lengths, or no dATP, was present in the reaction mixture.

The relative levels of incorporation of the modified nucleotides at the 90 minute time point are seen in Table 1 below, in which the data are reported as percent incorporation of the tracer radio-nucleotide ($^3$H-dGTP) relative to incorporation resulting from a reaction mixture containing dNTP's and no derivatives. Duplicate figures indicate two determinations. Results for dCTP and analogs appear also.

TABLE 1

| Nucleotide | % Incorporation (90 min.) |
|---|---|
| dATP | 100 |
| $N^6$—aminohexyldATP | 67, 75 |
| Biotin-7-dATP | 53, 59 |
| Biotin-14-dATP | 33, 39 |
| Biotin-3-dATP | 29, 23 |
| Biotin-10-dATP | 15, 17 |
| Biotin-10'-dATP | 6.9, 7.5 |
| Biotin-17-dATP | 6.7, 5 |
| no ATP | 6.5, 6 |
| dCTP | 100 |
| $N^4$—(6-aminohexyl)dCTP | 74 |
| Biotin-7-dCTP | 44 |
| Biotin-14-dCTP | 42 |
| Biotin-10-dCTP | 22 |
| Biotin-3-dCTP | 12 |

Figure 6:
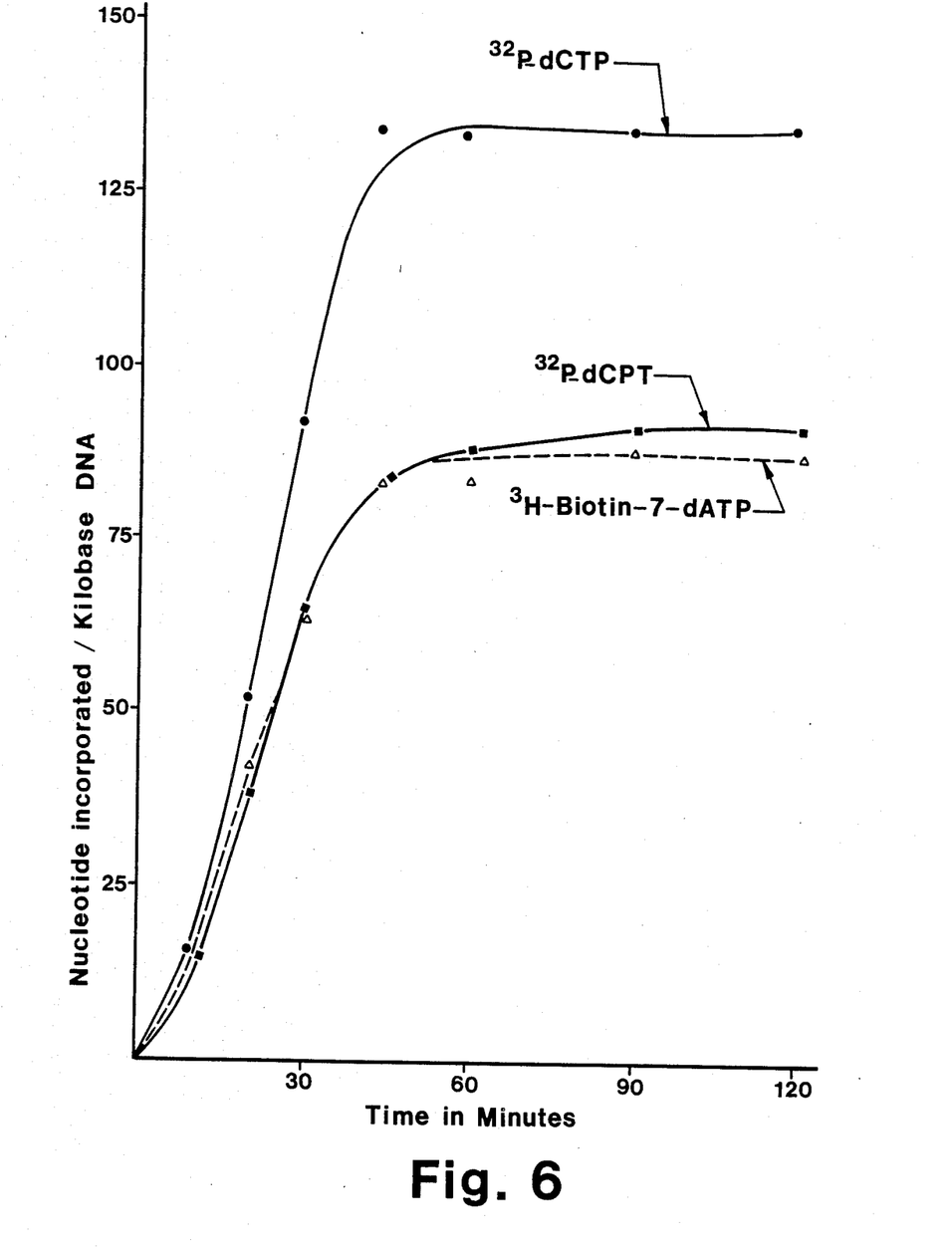
FIG. 6 is a graph showing nucleotide incorporation as measured by various radioactive labeling means.

Using the same protocol, incorporation was then performed using a radiolabelled biotin-nucleotide. Thus, the level of biotin incorporation was directly determined. 200 $\mu$l of the reaction mixture contained 10 $\mu$Ci of $\alpha$-$^{32}$PdCTP and either 20 $\mu$M dATP or 20 $\mu$M [$^3$H-biotin]-7-dATP. The upper curve of FIG. 6 shows the time course of incorporation of $^{32}$P-dCMP when dATP was used in the reaction mixture. The lower curves show the time courses of incorporation of $^{32}$P-dCMP and the tritium labelled and biotinylated derivative of dAMP. The close correspondence of these two curves indicates that the level of biotin incorporation is accurately reflected by $^{32}$P-dNMP incorporation.

Studies on Sensitivity of Detection

To examine the detection sensitivity of probes made from the biotinylated nucleotides of the present invention, incorporation of various levels of Bio-7-dATP into plasmid DNA was carried out by nick translation as previously disclosed.

The reaction volume was 1 ml. At 10 minutes, 30 minutes and 90 minutes, 200 μl of the reaction mixture was removed and the reaction quenched with 30 mM EDTA. The DNA from each sample was purified on a Sephade® G-50 column. Various picogram quantities of each sample, as seen in Table 2 below, were spotted on a nitrocellulose filter and checked for visualizabilit after use of BRL's DNA Detection System (a streptavidin-biotin alkaline phosphatase system) and dye development for 2 hours. In Table 2, "+" or "−" indicates the presence or absence, respectively, of visible spots; it can be seen that a high degree of sensitivity exists even with a relatively low level of biotin incorporation.

TABLE 2

| Time, min. | 90 | 30 | 10 |
|---|---|---|---|
| Bio-7-dAMP per Kb | 98 | 35 | 7 |
| 50 pg of sample | + | + | + |
| 20 pg of sample | + | + | + |
| 10 pg of sample | + | + | + |
| 5 pg of sample | + | + | + |
| 2 pg of sample | + | + | + |
| 1 pg of sample | + | + | − |
| 0 pg of sample | − | − | − |

Probes biotinylated with various linker lengths were then compared for sensitivity of detection. Plasmid DNA was nick translated according to the described protocol with Biotin-n-dATP, for n=7, 14, 3 or 10. The biotinylated DNA's were then purified from unincorporated nucleotides by gel filtration on Sephadex® G-50 in 1×SSC (0.15 M NaCl, 0.015 M sodium citrate) containing 0.1% SDS. The biotinylated DNA was diluted into 6×SSC containing 0.2 μg/μl sheared herring sperm DNA and spotted onto nitrocellulose paper in the range of 50 pg/5 μl to 1 pg/5 μl. After 30 minutes' incubation in the NBT/BCIP dye mixture of the BRL DNA Detection System, 2 pg spots of Bio-7, 14 or 10-dATP labeled probe and a 5 pg spot of Bio-3-dATP labeled probe were visible. After 1.5 hours, the 1 pg spot of each biotin-dATP-labeled probe was visible.

Likewise, probe labeled with Bio-10-dCTP exhibited 2 pg sensitivity after thirty minutes of detection, and the 1 pg spot was visible after 1.5 hours. Probe labeled with both Bio-7-dATP and Bio-10-dCTP was not detected with a higher sensitivity than probe labeled with either nucleotide individually.

Detection of Single-Copy Gene Sequences With the Nucleotides of the Present Invention A plasmid containing the 1.1 Kb Mst II fragment of the human β-globin gene in the Eco RI site of pBR322 (obtained from Dr. Y. W. Kan, UCSF) was nick translated with either Biotin-n-dATP in the presence of dTTP, dCTP, and dGTP, or Biotin-n-dCTP in the presence of dATP, dTTP, and dGTP. All nucleotides were at 20 μM and the reaction was allowed to proceed for 90 minutes. Conditions for nick translation of the DNA probe and purification of the biotin-labeled material are given in the manual of the BRL DNA Detection System.

The biotinylated probe was hybridizedto a Southern blot of Eco RI digested human DNA or to an Eco RI digest of the plasmid DNA. Probe concentration was 100 ng/ml and hybridization was allowed to proceed for 16–24 hours under conditions described by Leary et al. (Leary, J. J., Brigati, D. J. and Ward, D. C. (1983) *Proc. Natl. Acad. Sci. USA* 80 4045–4049). The filter was developed with the BRL Detection System as described in the system's instruction manual. The single copy β-globin gene Fragment at 5.2 Kb was observed within 3 hours of staining with the NBT/BCIP dye system for DNA probes labeled with Biotin-n-dATP where n=3, 7, 10 or 14 and Biotin-n-dCTP where n=7 or 10.

Thus, Biotin-n-dATP where n=3, 7, 10 or 14 and Biotin-n-dCTP where n=7 or 10 may be used to label a nucleic acid probe which will then recognize a single copy gene sequence in a Southern blot of genomic DNA. The annealed probe-target hybrid may then be detected by a commercially available DNA detection system.

Specific Example of Synthesis of Bio-7-dATP

Following is an example of the first described synthetic procedure, in which Bio-7-dATP was prepared:

1. Preparation of Biotin-N-hydroxysuccinimide

Biotin (1.0 g, 4.1 mmole) was dissolved in 10 ml DMF (dry) with heating at 80° C. in oil bath. CDI (665 mg, 4.1 mmoles) was added and the mixture was heated at 80° C. The reaction mixture was stirred at 80° C. for 30 minutes, then at room temperature for 2 hours; a white precipitate formed. N-hydroxysuccinimide (475 mg, 4.1 mmoles) was added and the reaction mixture was stirred at room temperature overnight. DMF was removed under vacuum on rotary evaporator. The solid residue was dissolved in 250 ml of refluxing isopropanol, filtered, and stored in the cold room overnight. The precipitate was filtered, washed one time with cold isopropanol and dried in vacuo at 45° C. overnight to give 870 mg (61% yield) of the desired product.

2. Preparation of 6-Chloropurine-2′-deoxyriboside

2′-Deoxyinosine (5.0 g, 0.02 M) in methylene chloride (100 ml) was cooled to 0° C. under nitrogen in a 3-neck 3 liter flask. Trifluoroacetic anhydride (45.0 g, 0.25 mole) was added and stirred for 2 hours. The temperature was allowed to rise to 15° C. and an aspirator was connected (a trap of drierite was used) and the major part of methylene chloride was removed at room temperature. A vacuum pump was attached and the residual trifluoroacetic anhydride and methylene chloride were removed (about 30 minutes). A foam was obtained at this stage.

The flask was fitted with a dropping funnel, a condenser and a gas dispersion tube inlet. Methylene chloride (500 ml) was added and the solution heated to a gentle reflux and a steady stream of nitrogen was bubbled through. A solution of freshly distilled thionyl chloride (16 ml) and DMF (8 ml) in methylene chloride (200 ml) was added dropwise during a 2 hour period. The reaction was refluxed for 5 hours (to overnight) cooled and filtered. An offwhite solid of 0.5 g hypoxanthine was obtained. The solution was slowly poured into a vigorously stirred ice cold solution of sodium bicarbonate (30 g) in 500 ml $H_2O$. The two phases were separated and the aqueous layer was extracted with two 250 ml portions of methylene chloride. The organic phase was combined, dried over sodium sulfate and concentrated. The resulting semisolid was dissolved in 10 ml methanol, applied to a column of neutral alumina (2.5 cm×40 cm, 75 g), and eluted with methanol. The first 75 ml was discarded and the column washed with 1 liter of methanol. The methanol was concentrated and the resulting solid crystalized from methanol/ethyl acetate (weight=3.8 g yield=70%, mp=138°-140° C.) HPLC analysis showed it to be a single compound.

3. 6-Chloropurine-2'-deoxyriboside 5'-monophosphate

Molecular Sieve (4 Å, 5.0 gm) was ground to give a coarse powder, added to triethyl phosphate (10 ml), and stirred vigorously for 10 minutes. The 6-chloropurine-2'deoxyriboside (135 mg) was added and the mixture cooled to 0° C. Phosphorous oxychloride (90 μl) was pretreated with water (9 μl) very carefully at 0° C. and added to the reaction mixture in one portion with an oven dry glass pipet or glass syringe. The reaction mixture was monitored on HPLC for the appearance of product and disappearance of starting material. After the complete disappearance of starting material the reaction mixture was filtered and added to 20 ml of ice water and the pH was adjusted to about 7.5 5 with 1 M TEAB. The solution was extracted with ether (4×50 ml).

The aqueous layer was concentrated on the rotary evaporator to remove any residual ether and diluted to 200 ml with water. It was applied to a Sephadex column ($HCO_3^-$ form, 70 ml, equilibrated with 0.01 M TEAB) and washed with 200 ml 0.01 M TEAB. It was then eluted with a gradient of 0.01 M to 0.5 M TEAB (400 ml each). 20 ml fractions were collected. Fractions 24-40 had UV active fractions; they were combined, concentrated, and coevaporated with ethanol (4×100 ml) to give a slightly brownish gum that weighed 245 mg (90%).

4. $N^6$-(6-aminohexyl)-2'-deoxyadenosine 5'-monophosphate

The diaminohexane (1.12 g) was dissolved in 5 ml $H_2O$ and the pH adjusted to about 9-9.5 with carbon dioxide. The 6-chloropurine-2'-deoxyriboside 5'-monophosphate (204 mg) in 5 ml $H_2O$ was added and the reaction mixture was heated at 50° C. and monitored on HPLC until the complete disappearance of the starting material (1.5-3 hours). It was cooled to room temperature, diluted to 200 ml with water, and loaded on Sephadex-A-25 column (70 ml, 2.5 cm×45 cm, $HCO_3^-$ form equilibrated with 0.01 M TEAB). The column was washed with 400 ml of 0.01 M TEAB followed with a gradient of 0.01 M to 0.5 M TEAB (350 ml each) and 20 ml fractions were collected. Fractions 10-20 contained the desired compound, which was concentrated and coevaporated with ethanol (4×100 ml) to give an off-white solid that weighed 184 mg (70%). HPLC analysis showed it to be a single peak.

5. $N^6$-(6-hexylamidobiotin-2'-deoxyadenosine 5'-monophosphate 6-aminohexyldAMP (80 mg) was dissolved in 0.1 M sodium borate (10 ml, pH 8.5). Biotin-NHS was dissolved in DMF (1.5 ml) and added to the amine. The mixture was stirred vigorously until HPLC analysis showed the disappearance of the starting material (1-4 hours). The reaction mixture was concentrated to remove the DMF and then dissolved in 100 ml of water and loaded onto a Sephadex-A-25 column ($HCO_3^-$ form, 30 ml, 1.5 cm×40 cm). The column was washed with 100 ml 0.01 M TEAB. It was then eluted with a gradient 0.1 M to 0.5 M TEAB (300 ml each); 18 ml fractions were collected. The desired compound eluted in fractions 20-25. The fractions were combined and concentrated and coevaporated with ethanol (4×100 ml) to give a white solid that weighed 90 mg (81%). It was a single compound on HPLC analysis and was positive for biotin.

6. $N^6$-(6-hexylamidobiotin)-2'-deoxyadenosine 5'-triphosphate (bio-7-dATP)

Bio-7-dAMP (45 mg) was coevaporated with anhydrous DMF (3×10 ml) and finally dissolved in 2 ml DMF. Carbonyldiimidazole (40 mg) was added and the flask was tightly stoppered and vigorously stirred for about 1 hour. HPLC analysis revealed the starting material was consumed. (Reaction is stopped when the starting material is completely consumed. This may take 30 minutes to about 2 hours). 15 μl of methanol was added and stirring continued for 30 minutes. Tributylammonium pyrophosphate (1.3 ml of 89 mg/ml DMF solution) was added and stirring continued overnight. The material was filtered. The filtrate was concentrated and then diluted to 100 ml with $H_2O$ and loaded on Sephadex-A-25 ($HCO_3^-$ form, 30 ml 1.5×30 cm). It was washed with 100 ml 0.01 M TEAB followed with a gradient of 0.01 M to 0.5 M TEAB (200 ml each) and then 200 ml each of 0.5 M and 1.0 M TEAB. 20 ml fractions were collected. Fractions 30-38 contained the desired compound which weighed 40 mg (56%). It was a single compound on HPLC.

The invention has been described in detail with particular emphasis on the preferred embodiments thereof, but it should be understood that variations and modifications within the spirit and scope of the invention may occur to those skilled in the art to which the invention pertains.

We claim:

1. In the process of detecting the presence of a target polynucleotide, said process comprising incorporating a deoxyribonucleotide, modified by the attachment thereto of a biotin, into a polynucleotide complementary to said target polynucleotide;

hybridizing said complementary polynucleotide to said target polynucleotide; and detecting the presence of said biotin;

the improvement comprising using, for said modified deoxyribonucleotide, compound of the form (d)BTP—NH—L—X, where

TP represents triphosphate, and (D)BTP represents dATP, dCTP, dGTP, 3'-deoxy ATP, 3'-doexy CTP, 3'-deoxy GTP, 2',3'-dideoxy ATP, 2',3'-dideoxy CTP or 2',3'-dideoxy GTP;

L is bonded through the N of NH to the $N^6$ position of B when B represents adenosine, to the $N^4$ position of B when B represents cytidine, and to the $N^2$ position of B when B represents guanosine;

L presents either
$(CH_2)_n$, where $1 \leq n \leq 12$,
$(CH_2)_n NH—CO—(CH_2)_m$, where $2 \leq n+m \leq 24$,
$(CH_2)_n O—CO—(CH_2)_m$, where $2 \leq n+m \leq 24$,
or
$(CH_2)_n S—CO—(CH_2)_m$, where $2 \leq n+m \leq 24$;
and X represents where Y represents either NH, O, or S.

2. The improved process of claim 1 and in which (d)BTP represents dATP or dCTP.

3. The improved process of claim 1 and in which (d)BTP represents dGTP.

4. The improved process of claim 1 and in which L represents either $(CH_2)_n$ for an n such that $1 \leq n \leq 12$, or $(CH_2)_n NHCO(CH_2)_m$ for an n and m such that $2 \leq n+m \leq 24$.

5. In the process of detecting the presence of a target polynucleotide, said process including incorporating a deoxyribonucleotide into a polynucleotide complementary to said target polynucleotide, and hybridizing said complementary polynucleotide to said target polynucleotide, the improvement comprising, using, for said deoxyribonucleotide, a compound of the form (d)BTP—NH—M, where TP represents triphosphate, and (d)BTP, represents dATP, dCTP, dGTP, 3'-deoxy ATP, 3'-deoxy CTP, 3'-deoxy GTP, 2',3'-dideoxy ATP, 2',3'-deoxy CTP or 2',3'-didexoy GTP;

M is bonded through the N of NH to the $N^6$ position of B when B represents adenosine, to the $N^4$ position of B when B represents cytidine, and to the $N^2$ position of B when B represents guanosine; and M represents a compound of the form L-X, where X represents $NH_2$, OH or SH, and L represents either $(CH_2)_n$ for an n such that $1 \leq n \leq 12$, or $(CH_2)_n NHCO(CH_2)_m$ for an n and m such that $2 \leq n+m \leq 24$.

6. The improved process of claim 5 and in which (d)BTP represents dATP or dCTP.

7. The improved process of claim 5 and in which (d)BTP represents dGTP.

8. The improved process of claim 5 and in which X represents $NH_2$.

9. A compound having the structure

(d)BTP—NH—L—NH—X wherein
(a) TP represents triphosphate, and (d)BTP represents either 2'-deoxy BTP, 3'-deoxy BTP, or 2',3'-dideoxy BTP, and B represents adenosine, cytidine or guanosine;
(b) when B represents adenosine or guanosine, L is bonded through NH to the $N^6$ position of adenosine or the $N_2$ position of guanosine, and L represents either $(CH_2)_n$ for an n such that $1 \leq n \leq 12$, $(CH_2)_n NHCO(CH_2)_m$ for an n and m such that $2 \leq n+m \leq 24$, $CH_2CONH(CH_2)_5$ for $1 \leq n \leq 12$, or $CH_2CONH(CH_2)_n NHCO(CH_2)_5$ for $1 \leq n \leq 12$;
(c) when B represents cytidine, L is bonded through NH to the $N^4$ position of B and L represents either $(CH_2)_n$ for an n such that $1 \leq n \leq 12$ or $(CH_2)_n NHCO(CH_2)_m$ for an n and m such that $2 \leq n+m \leq 24$, and
(d) X represents biotin.

10. The compound of claim 9 and wherein B is either adenosine or cytidine.

11. The compound of claim 9 and wherein (d)BTP is either dATP or dCTP.

12. A compound having the structure, wherein
(a) TP represents triphosphate, and (d)R represents 2'-deoxyribose, 3'-deoxyribose or 2', 3'-dideoxyribose; and either
(b) B represents either adenine or cytosine and L represents either $(CH_2)_n$ where $1 \leq n \leq 12$, or $(CH_2)_n NHCO(CH_2)_m$, where $2 \leq n+m \leq 24$, or
(c) B represents adeine and L represents either $CH_2CONH(CH_2)_n$ for $1 \leq n \leq 12$ or $CH_2CONH(CH_2)_n NHCO(CH_2)_5$ for $1 \leq n \leq 12$;
and wherein, when B represents adenine, L is covalently bonded through NH to the $N^6$ psition of B, and when B represents cytosine, L is covalently bonded through NH to the $N^4$ position of B.

* * * * *